United States Patent [19]

Jen et al.

[11] Patent Number: 4,894,806

[45] Date of Patent: Jan. 16, 1990

[54] ULTRASONIC IMAGING SYSTEM USING BUNDLE OF ACOUSTIC WAVEGUIDES

[75] Inventors: Cheng K. Jen, Brossard; Gerald W. Farnell, Montreal, both of Canada

[73] Assignee: Canadian Patents & Development Ltd., Ottawa, Canada

[21] Appl. No.: 12,279

[22] Filed: Feb. 9, 1987

[30] Foreign Application Priority Data

Apr. 3, 1986 [CA] Canada .................................. 505801

[51] Int. Cl.$^4$ ............................................. G03B 42/06
[52] U.S. Cl. ......................................... 367/7; 367/103; 73/625
[58] Field of Search .................. 367/138, 150, 7, 103; 358/112; 73/625, 609, 617; 181/176; 333/249, 157, 141-149

[56] References Cited

U.S. PATENT DOCUMENTS

| | | | |
|---|---|---|---|
| 2,225,312 | 12/1940 | Mason | 181/176 |
| 3,903,990 | 9/1975 | Tannaka | 367/150 |
| 3,922,622 | 11/1975 | Boyd et al. | 333/145 |
| 3,957,134 | 5/1976 | Daniel | 181/176 |
| 4,077,023 | 2/1978 | Boyd et al. | 333/147 |
| 4,091,387 | 5/1978 | Profera | 342/754 |
| 4,296,482 | 10/1981 | Kritz | 367/150 X |
| 4,743,870 | 5/1988 | Jen et al. | 333/147 |

FOREIGN PATENT DOCUMENTS

| | | | |
|---|---|---|---|
| 1030522 | 1/1951 | France | 333/249 |
| 843037 | 6/1981 | U.S.S.R. | 333/249 |

OTHER PUBLICATIONS

"Precision Waveguides"; Robert N. Marshall et al.; Western Electric The Engineer; Jan. 1957, vol. 1, No. 1; pp. 35-42.
"Lines, Waves and Antennas"; Robert Brown et al.; 1973, John Wiley & Sons; p. 239.

Primary Examiner—Thomas H. Tarcza
Assistant Examiner—Tod Swann
Attorney, Agent, or Firm—Yoshiharu Toyooka

[57] ABSTRACT

An ultrasonic imaging system for transmitting ultrasonic pulses into an object and detecting reflected ultrasonic waves therefrom. The system is provided with delay lines for real time imaging. The system comprises a probe means having a transmitting bundle of acoustic waveguides for transmitting ultrasonic pulses into an object. The transmitting bundle includes the delay lines which consists of having cladded acoustic waveguides of different lengths for introducing different delays in the ultrasonic pulses carried by each waveguide.

7 Claims, 2 Drawing Sheets

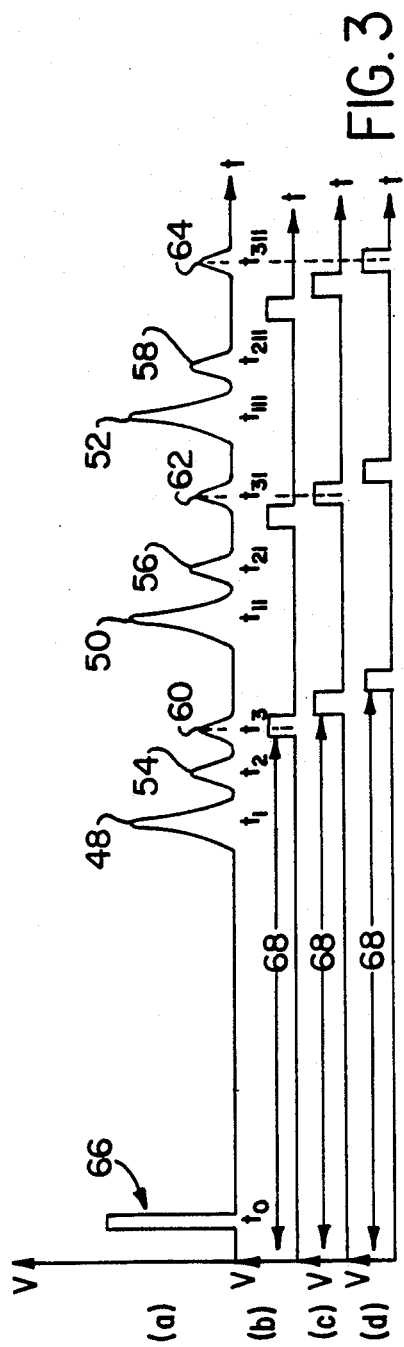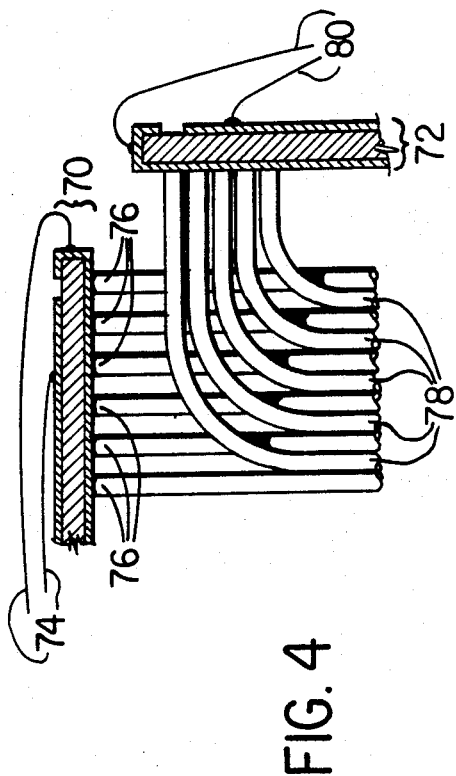

ULTRASONIC IMAGING SYSTEM USING BUNDLE OF ACOUSTIC WAVEGUIDES

FIELD OF THE INVENTION

The invention generally relates to ultrasonic imaging systems for testing sample by non-destructive pulse echo test method. More specifically, the invention is concerned with the provision of delay lines for real time imaging.

DESCRIPTION OF THE PRIOR ART

There have been a number of devices for providing delay lines in ultrasonic imaging system. Known in the art is an ultrasonic imaging system having variable delay lines (U.S. Pat. No. 4,267,584, May 12, 1981 McKeighen). The system comprises a plurality of analog shift register memory deivces, permutation means for sequencing and permuting information storage and retrieval to and from the memory devices such that the information storage and retrieval may be independently operated and time modifying means for altering the time interval between the operations of information storage and retrieval to produce dynamic variation of system delay.

Also known in the art is an ultrasonic imaging system having a linear array of transducer elements (U.S. Pat. No. 4,180,790, Dec. 25, 1979, Thomas). The apparatus is specifically concerned with single sector scanner, the array aperture of the system being increased as the range from which echoes are being received increases by effectively switching in more array elements by steps during every echo reception period. The dynamic aperture control and the dynamic focus control of the system are combined for adjusting time delays in the echo system processing channels to focus the echo at a plurality of focal points at different ranges.

Also known in the art is another ultrasonic imaging system having a linear array of ultrasonic transducers (U.S. Pat. No. 4,334,432, June 15, 1982, Gill). The apparatus is concerned with the focussing and steering of acoustic beams by using linked delay lines connected to the array of transducers, when the transducers operate in a receive mode, with delay values which are both linear and quadratic values of the distance of the respective transducer from the center of the array.

Although all the above systems are suitable for providing delay lines, all the above systems require sophisticated electronic components which are expensive and involve complicated circuitry, they also require a certain distance in between the acoustic transducers and the tested area of an object for providing focussing effect therefore image of the object can only be observed in certain distance from the acoustic transducers. They also require liquid coupling medium in between the object and the acoustic transducers.

There are needs for an ultrasonic imaging system for testing an object by non destructive pulse echo test method provided with simple and inexpensive delay lines, there is also a need for imaging the area of an object adjacent to the acoustic transducers and there is still a need for coupling the acoustic transducers with an object without liquid medium.

SUMMARY OF THE INVENTION

According to the present invention there is provided an ultrasonic imaging system for transmitting ultrasonic pulses into an object and detecting reflected ultrasonic waves from the object comprising:

electrical pulse generator means for producing electrical pulses;

transducer means for converting the electrical pulses to ultrasonic pulses and also converting the reflected ultrasonic waves to electrical signals;

probe means for transmitting the ultrasonic pulses into the object and detecting the reflected ultrasonic waves from the object, the probe means having a bundle of cladded acoustic waveguides, each of the acoustic waveguides having a core made of a solid or a liquid material and a solid cladding thereabout, the bulk longitudinal and shear wave velocities of the material of the core being smaller than those of the material of the cladding and each of the acoustic waveguides further having a different predetermined delay characteristic means for introducing different delays in the ulrasonic pulses carried by each waveguide; and display means for displaying acoustic discontinuities of the object in response to the electrical signals.

BRIEF DESCRIPTION OF THE DRAWINGS

The accompanying drawings illustrate, by way of example, embodiments of the present invention, in which

FIG. 3 shows, by way of example, a waveform diagram of electric signals indicative of ultrasonic waves detected by the ultrasonic transducer probe of FIG. 2; and FIG. 4 shows alternative embodiments of the transducer means and the probe means according with the present invention.

DETAILED DESCRIPTION OF THE DRAWINGS

Figure 1:
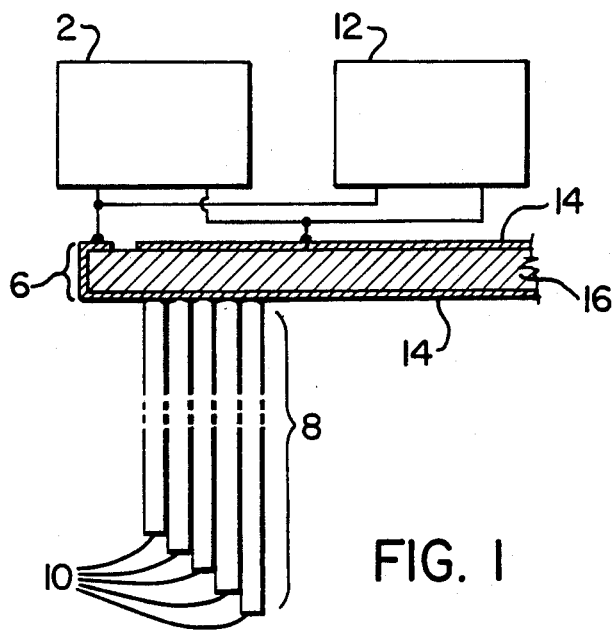
FIG. 1 shows an ultrasonic image system according with the present invention.

In FIG. 1, there is shown an ultrasonic imaging system for transmitting ultrasonic pulses into an object and detecting reflected ultrasonic waves from the object comprising:

electrical pulse generator 2 means for producing electrical pulses;

transducer means 6 for converting the electrical pulses to ultrasonic pulses and also converting the reflected ultrasonic waves to electrical signals;

probe means 8 for transmitting the ultrasonic pulses into the object and detecting the reflected ultrasonic waves from the object, the probe means 8 having a bundle of cladded acoustic waveguides 10, the bundle having a delay means for introducing different delays in the ultrasonic pulses carried by each waveguide; and display means 12 for displaying acoustic discontinuities of the object in response to the electrical signals.

The delay means is made of waveguides 10 having different lengths so that different delays are introduced in the ultrasonic wave pulses carried by each waveguide. The bundle is connected to both the display means 12 and the electrical pulse generator means 2 via a transducer means 6 for transmitting the pulses into the object and detecting reflected ultrasonic waves by the object.

Cladded acoustic waveguides 10 having a core and cladding regions made of doped or pure fuse silica can be used for transmitting ultrasonic wave pulses and detecting ultrasonic waves. Ultrasonic wave pulses are directly transmitted to all the waveguides 10 simultaneously. Transducer means 6 is a thin piezo-electric crystal 16 placed in between two electrodes 14. The bundle is coupled to the transducer means 6 at one end and pointed at the object at the other end. The waveguides 10 can be fused together if they are made of glass type material, they can also be glued or bound together.

Cladded acoustic waveguides with core and cladding regions having weakly guiding conditions are preferred, these weakly guiding conditions for shear mode operation are $$0 < \frac{(V_{s2} - V_{s1})}{V_{s1}} << 1$$

where $V_{s1}$ and $V_{s2}$ are respectively the bulk shear wave velocities of the core and cladding regions, and $$\left| \frac{\rho_2 - \rho_1}{\rho_1} \right| << 1$$

where $\rho_1$ and $\rho_2$ are respectively the material densities of the core and cladding regions.

The weakly guiding conditions for longitudinal mode operations are $$\left| \frac{(V_{s2} - V_{s1})}{V_{s1}} \right| << 1,$$

$$\left| \frac{\rho_2 - \rho_1}{\rho_1} \right| << 1$$

$$\text{and } 0 < \frac{V_{L2} - V_{L1}}{V_{L1}} << 1$$

where $V_{L1}$ and $V_{L2}$ are respectively the bulk longitudinal wave velocities of the core and cladding regions.

If the ultrasonic pulses have to travel in liquid medium then only longitudinal mode can be used.

When longitudinal mode operation is used, a transducer means for longitudinal mode is required and when shear mode operation is used, a transducer means for shear mode is required.

An alternative embodiment of the delay means has a bundle of acoustic waveguides with equal lengths and the waveguides of the bundle are made of different materials so that velocity of ultrasonic pulses in each waveguide is different therefore different delays are introduced in the ultrasonic pulses carried by each waveguide. The different materials are produced by using doped fused silica glass with different amount of dopant concentration in each waveguide.

Figure 2:
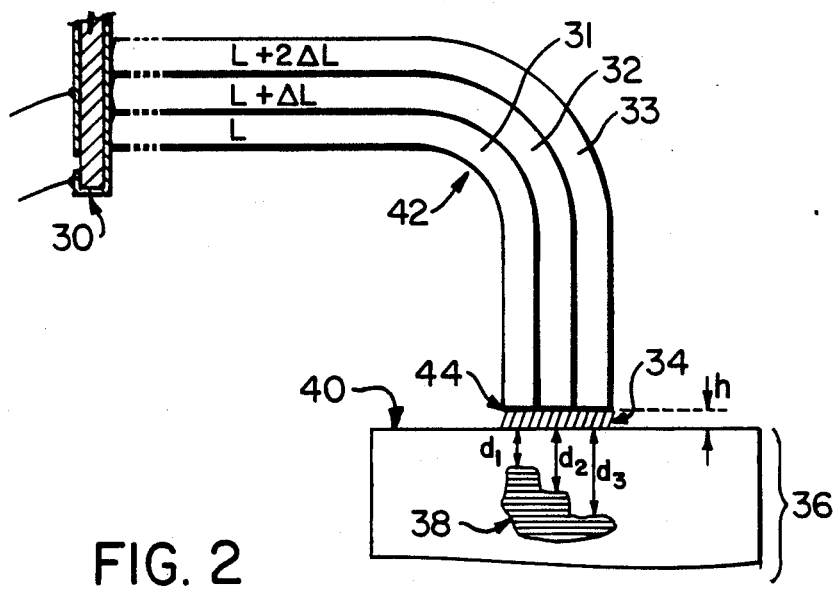
FIG. 2 shows the ultrasonic transducer probe of FIG. 1 in relation with an object.

FIG. 2 shows an embodiment of an ultrasonic transducer probe according with the present invention in relation with an object 36. A bundle of cladded acoustic waveguides 31, 32 and 33 is coupled at one end to a piezo-electric transducer 30 and aimed at the object 36 at the other end. The waveguides have different lengths, the length of the first waveguide 31 is L, the second waveguide 32 is $L + \Delta L$ and the third waveguide is $L + 2\Delta L$ where $\Delta L$ is approximately 1.25 mm and L is substantially larger than $\Delta L$.

A curve 42 is shaped along the length of the bundle and waveguides 31, 32 and 33 forming an array are disposed in size order within the array, the shortest waveguide 31 being in the inside portion of the curve 42 and the longest waveguide being in the outside portion of the curve 42 so that end surfaces of the bundle are uniform. A coupling medium separates bundle end 44 from the surface 40 of the object 36 by a distance of h. A sub-surface crack 38 of the object is shown, the distance between the waveguides 31, 32 and 33 and the sub-surface crack are respectively $d_1$, $d_2$ and $d_3$. The piezo-electric transducer 30 transmits ultrasonic wave pulses in the waveguides 31, 32 and 33; the pulses pass through the coupling layer 34, into the object 36 and then reach the sub-surface crack 38. Ultrasonic waves are reflected each time that a pulse meets an acoustic discontinuity.

FIG. 3 shows waveform diagrams of electric signals reepresentative of ultrasonic waves detected by the ultrasonic transducer probe of FIG. 2.

The vertical axis represent the voltage amplitude of the electric signal and the horizontal axis represent the time.

Electric signals 48, 50 and 52 situated at $t_1$, $t_{11}$ and $t_{111}$ are representative of the reflected waves detected respectively by the waveguides 31, 32 and 33 and generated when the pulse 66 transmitted at $t_0$ meets the coupling layer 34. Electric signals 54, 56 and 58 situated at $t_2$, $t_{21}$ and $t_{211}$ are representative of the reflective waves detected respectively by the waveguides 31, 32 and 33 and generated when the pulse 66 transmitted at $t_0$ meets the surface 40 of the object 36. Electric signals 60, 62 and 64 situated at $t_3$, $t_{31}$ $t_{311}$ are representative of the reflected waves detected respectively by the waveguides 31, 32 and 33 and generated when the pulse 66 transmitted at $t_0$ meets the sub-surface crack 38 situated respectively at distance $d_1$, $d_2$ and $d_3$ from the waveguides 31, 32 and 33.

The time values shown on the diagram can be calculated with the following equations:

$$t_1 = \frac{2L}{v_1}$$

where $v_1$ is the speed of the ultrasonic pulses in the waveguides, $$t_{11} = \frac{2(L + \Delta L)}{v_1},$$

$$t_{111} = \frac{2(L + 2\Delta L)}{v_1},$$

$$t_2 = t_1 + \frac{2h}{v_2}$$

where $v_2$ is the speed of the ultrasonic pulses in the coupling layer 34 and h the thickness of the layer, $$t_{21} = t_{11} + \frac{2h}{v_2},$$

$$t_{211} = t_{111} + \frac{2h}{v_2},$$

$$t_3 = t_2 + \frac{2d_1}{v_3}$$

where $v_3$ is the speed of the ultrasonic pulses within the object 36, $$t_{31} = t_{21} + \frac{2d_2}{v_3} \text{ and,}$$

$$t_{311} = t_{211} + \frac{2d_3}{v_3}.$$

Each acoustic waveguide not only detects refleted waves resulting from pulses transmitted by itself, it also detects reflected waves resulting from pulses transmitted by adjacent waveguides; but in this latter case the reflected waves are much more weak so that electric signals representative of these weak waves are eliminated as noise.

It is possible to study acoustic discontinuities situated at one particular depth of the object by processing the electrical signals with gating pulses. By varying the delay 68 of the gating pulses shown on (a), (c) and (d) of FIG. 3 it is possible to vary the depth of the object under examination. The repetition rate of the gating pulses is selected to be $2\Delta L/v_1$ so that electrical signals for one particular depth are sampled from all the waveguides of the bundle.

In FIG. 3 there are shown proper gating pulses (b), (c) and (d) for studying acoustic discontinuities situated respectively at depth of $d_1$, $d_2$ and $d_3$.

Repetition rate of the gating pulses corresponds to scanning speed of ultrasonic imaging system.

With a $\Delta L$ of the order of 1.25 mm and $v_1$ being approximately 5000 m/s, the scanning speed, $2\Delta L/v_1$, of the imaging system is 0.5 μs.

It should be noted that for real time image (30 frame/s) composed of 256 by 256 points, the scanning time $(1/30 \times 256 \times 256)$ of each point is 0.5 μs at most. If the delay 68 is adjusted at time $t_2$ then the acoustic discontinuities detected are representative of the elastic profile of the surface of the object.

In FIG. 4, there is shown alternative embodiments of the transducer means and the probe means according with the present invention.

The transducer means has a first transducer 72 for converting the electrical pulses to ultrasonic pulses and a second transducer 70 for converting the ultrasonic waves to electrical signal. The probe means has a transmitting bundle 78 of cladded acoustic waveguides for transmitting the ultrasonic pulses into the object and a detecting bundle 76 for detecting the reflected ultrasonic waves from the object; the transmitting bundle 78 having a delay means for introducing different delays in the ultrasonic pulses carried by each waveguide.

The first transducer is connected to an electrical pulse generator by two leads 80 and the second transducer is also connected to a display means by two leads 74.

An alternative embodiment of the delay means shown on FIG. 4 has a transmitting bundle of acoustic waveguides with equal lengths and the waveguide of the transmitting bundle are made of different materials so that different delays are introduced in the ultrasonic pulses carried by each waveguide.

We claim:

1. An ultrasonic imaging system for transmitting ultrasonic pulses into an object and detecting reflected ultrasonic waves from the object comprising:

electrical pulse generator means for producing electrical pulses;

transducer means for converting the electrical pulses to ultrasonic pulses and also converting the reflected ultrasonic waves to electrical signals;

probe means for transmitting the ultrasonic pulses into the object and detecting the reflected ultrasonic waves from the object, the said probe means having a bundle of cladded acoustic waveguides, each of the acoustic waveguides having a core made of solid or a liquid material and a solid cladding thereabout, the bulk longitudinal and shear wave velocities of the material of the core being smaller than those of the material of the cladding, and each of the said acoustic waveguides further having a different predetermined delay characteristic for introducing different delays in the ultrasonic pulses carried by each waveguide in that each of the said acoustic waveguides receives substantially only the reflected ultrasonic waves resulting from pulses transmitted by itself; and display means for displaying acoustic discontinuities of the object in response to the electrical signals.

2. An ultrasonic imaging system as defined in claim 1 wherein the said bundle comprises waveguides of different lengths for introducing different delays in the ultrasonic wave pulses carried by each waveguide.

3. An ultrasonic imaging system as defined in claim 1 wherein the said bundle comprises waveguides whose claddings and cores are made of different materials for introducing different delays in the ultrasonic wave pulses carried by each waveguide.

4. An ultrasonic imaging system as defined in claim 2 wherein the bundle of waveguides is further defined by having two end surfaces situated at each extremity of the bundle and a curve shaped along the length of the bundle, the waveguides forming an array are disposed in size order within the array, the shortest waveguide being in the inside portion of the curve and the longest waveguide being in the outside portion of the curve whereby the end surfaces of the bundle are uniform.

5. An ultrasonic imaging system for transmitting ultrasonic pulses into an object and detecting reflected ultrasonic waves from the object comprising:

electrical pulse generator means for producing electrical pulses;

transducer means having a first transducer for converting the electrical pulses to ultrasonic pulses and a second transducer for converting the ultrasonic waves to electrical signals;

probe means having a transmitting bundle of acoustic waveguides for transmitting the ultrasonic pulses into the object and a detecting bundle of acoustic waveguides for detecting the reflected ultrasonic waves from the object, each of the acoustic waveguides of the both bundles having a core made of a solid or a liquid material and a solid cladding thereabout, the bulk longitudinal and shear wave velocities of the material of the core being smaller than those of the material cladding, and each of the said acoustic waveguides in the transmitting bundle further having a different predetermined characteristic for introducing different delays in the ultrasonic pulses carried by each waveguide in that each of the said acoustic waveguides in the detecting bundle receives substantially only the reflected ultrasonic waves resulting from pulses transmitted by itself; and display means for displaying acoustic discontinuities of the object in response to the electrical signals.

6. An ultrasonic imaging system as defined in claim 5 wherein the said transmitting bundle comprises waveguides of different lengths for introducing different delays in the ultrasonic wave pulses carried by each waveguide.

7. An ultrasonic imaging system as defined in claim 5 wherein the said transmitting bundle comprises waveguides whose claddings and cores are made of different materials for producing different delays in the ultrasonic wave pulses carried by each waveguide.

* * * * *